United States Patent [19]

De Vaughn

[11] Patent Number: 5,662,127
[45] Date of Patent: Sep. 2, 1997

[54] SELF-CONTAINED BLOOD WITHDRAWAL APPARATUS AND METHOD

[75] Inventor: Donald H. De Vaughn, San Francisco, Calif.

[73] Assignee: Bio-Plas, Inc., San Francisco, Calif.

[21] Appl. No.: 582,334

[22] Filed: Jan. 17, 1996

[51] Int. Cl.$^6$ .............................. A61B 5/00; A61B 17/14
[52] U.S. Cl. ............................................. 128/765; 606/181
[58] Field of Search ..................................... 604/162, 167, 604/192, 198; 606/181–182, 197, 198, 110; 128/635, 760, 765–766, 754, 752, 758, 761, 763, 764, 770, 919; 422/61; 204/403, 409, 433, 406, 416, 435, 422

[56] References Cited

U.S. PATENT DOCUMENTS

| | | | |
|---|---|---|---|
| 4,616,649 | 10/1986 | Burns | 128/314 |
| 4,828,547 | 5/1989 | Sahi et al. | 604/110 |
| 4,889,117 | 12/1989 | Stevens | 606/181 |
| 5,026,388 | 6/1991 | Ingalz | 606/182 |
| 5,284,570 | 2/1994 | Savage et al. | 204/422 |
| 5,330,439 | 7/1994 | Jackson | 604/192 |
| 5,342,320 | 8/1994 | Cameron | 604/192 |
| 5,368,047 | 11/1994 | Suzuki et al. | 128/765 |
| 5,395,347 | 3/1995 | Blecher et al. | 604/192 |
| 5,527,334 | 6/1996 | Kanner et al. | 606/182 |

*Primary Examiner*—Michael Buiz
*Assistant Examiner*—Nancy Connolly Mulcare
*Attorney, Agent, or Firm*—Flehr Hohbach Test Albritton & Herbert LLP

[57] ABSTRACT

A self-contained blood withdrawal apparatus (20) which includes a movable appendage piercing mechanism (27), a suction mechanism (30) and a specimen storage container (29). A base portion (21) is formed with a cavity opening (24) over which the appendage (10) is placed and a first passageway (25) extending from the opening to the storage container. The appendage piercing mechanism (27) is aligned with the cavity opening (24) and is movable between a retracted position and an extended appendage piercing position. Additionally, the suction mechanism (30), for facilitating withdrawal of the blood from the appendage, is coupled to the base portion (21) and communicates with the cavity opening through a second passageway (31). Accordingly, present invention provides a unitary apparatus which pierces an appendage, facilitates blood withdrawal and stores the specimen in a container.

22 Claims, 8 Drawing Sheets

SELF-CONTAINED BLOOD WITHDRAWAL APPARATUS AND METHOD

TECHNICAL FIELD

The present invention relates, generally, to blood withdrawal devices and methods and, more particularly, to lancet and blood specimen assemblies for blood withdrawal.

BACKGROUND ART

Typically, blood withdrawal from the body, for donations or test purposes, is performed with a syringes by inserting a needle into the median cubital vein between the biceps and the forearm muscles of the arm. This technique, of course, is a relatively simple procedure which usually employs a vacuum tube insert to store the blood and which facilitates withdrawal of blood through the suction created by the vacuum tube. Without the assistance of a vacuum, blood pressure alone is generally insufficient to extract large quantities of blood in a short time span. This procedure, however, often cannot be performed on infants, smaller children, elderly individuals, or the extremely ill because their physical stature prevent withdrawal of large quantities of blood. Moreover, many blood testing procedures do not require large volume blood specimens.

Consequently, blood lancets were developed as a means for extracting capillary blood which is most commonly withdrawn from the fingertips. Approximately 4 million of these procedures are performed yearly in the United States. These blood specimens facilitate screening tests and supply blood from those who can ill-afford furnishing large quantities.

Originally, blood lancets were merely plates having a surgical blade extending therefrom formed to pierce the fingertip using a jabbing motion. Typical of such devices is the Bard Parker surgical blade. These crude blades frighten children and adults alike.

More recently, the blood lancet has evolved into elongated plastic devices which include a piercing needle or blade protruding from one end thereof. Typically, the technician holds the patient's hand, with the palm facing upward, and jabs the fingertip with the needle in a motion similar to the Parker blade. When the finger starts to bleed, the technician places a vial or blood absorbing blotter adjacent the perforation and extracts the blood by squeezing the fingertip. When more than a few drops of blood are to be withdrawn, this procedure is performed until approximately 750 microliters of blood are collected in the vial, upon which the vial is closed, and subsequently, tested.

One problem associated with this technique is that the overall procedure is inaccurate and cumbersome. The patient must rely on the technician's accuracy in jabbing their finger. The medical technician, may miss the target area, which will require piercing the finger twice in order to withdraw the properly needed amount. Subsequently, the technician is required to separately hold the vial against the finger to gravitationally capture the blood secreted from the perforation while simultaneously pressurizing the finger. This combination is rather clumsy and may result in spillage of the specimen or dropped vials. Not only does this waste time and burden the patient, the specimen may potentially be contaminated as well.

Another problem associated with this procedure and the blood lancet itself is that it exposes the medical technician to contact with the donor's blood. The issue of accidental sticks and also of aerosolized blood has come to the forefront of concern first as a result of hepatitis caused by cross contamination and yet more recently by the advent of the very serious worldwide epidemic of acquired immune deficiency syndrome (AIDS). Many efforts are being made around the world to minimize the possibility of health care workers being accidentally contaminated by sticks from sharp instruments such as cutting implements, hypodermic needles and finger lancets. For instance, it is now common procedure for the medical technician to wear protective gloves whenever handling blood or instruments coming in contact with blood.

While these gloves provide greater protection to the technician, contact with the patient's blood is common. Moreover, the exposed lancet still poses an unsafe and unsanitary threat. Accidental sticks by the lancet easily pierce the glove and skin so that the medical technician must practice an abundance of caution when handling these devices.

This problem has been overcome by providing a spring mechanism which cooperates with the lancet to withdraw it into a receptacle after puncture of an appendage. Hence, exposure to an unsafe and unsanitary lancet is minimized. Subsequent to puncture and withdrawal of the lancet, however, the technician is still required to separately hold a vial against the finger to gravitationally capture the blood secreted from the perforation while simultaneously pressurizing the finger. Contact with the blood flowing from the perforation is still poses an immediate hazard. Typical of such spring-loaded lancets are disclosed in U.S. Pat. No. 4,616,649 to Burns; and U.S. Pat. No. 5,026,388 to Ingalz.

Accordingly, it is an object of the present invention to produce a self-contained blood withdrawal apparatus and method which promotes safety of use.

It is another object of the present invention to provide a self-contained blood withdrawal apparatus and method which reduces patient pain, apprehension and trauma.

Still another object of the present invention is to provide a self-contained blood withdrawal apparatus and method which punctures the skin on the first attempt and more accurately pierces the designated area.

Yet another object of the present invention is to provide a self-contained blood withdrawal apparatus and method which facilitates removal and storage of the specimen.

It is a further object of the present invention to provide a self-contained self-contained blood withdrawal apparatus and method which is durable, compact, easy to maintain, has a minimum number of components, is easy to use by unskilled personnel, and is economical to manufacture.

DISCLOSURE OF INVENTION

The present invention includes a self-contained blood withdrawal apparatus for an appendage comprising a base portion having a platform. This platform includes an upper surface which defines a recess therein. Further, the base portion is formed with a passageway extending from the recess. An appendage piercing mechanism formed for drawing blood from an appendage, such as a finger, is disposed in the recess and is movable between a retracted position and an extended appendage piercing position. Further, the apparatus includes an operating mechanism positioned relative to the piercing mechanism for moving the piercing mechanism between the retracted and extended positions. A storage container for storing withdrawn blood is releasably coupled to the base portion and communicates with the recess through the passageway. Additionally, a mechanism for facilitating withdrawal of the blood from the appendage is coupled to the base portion and communicates with the recess through the passageway.

In another aspect of the present invention, a piercing mechanism is provided for piercing the skin to draw blood from a patient. The piercing mechanism includes a base portion having a wall which defines a cavity and an opening into said cavity. A resilient, fluid impermeable diaphragm is positioned over the cavity opening in a manner preventing the drawn blood from flowing through the opening into the cavity. A piercing element is movably disposed in the cavity which cooperates with an operating assembly to move the piercing element from a retracted position, out of contact with the diaphragm, to a piercing position. In the piercing position, the piercing element extends through a hole in the diaphragm caused by the piercing element to pierce the skin proximate the cavity opening. Subsequently, the operating assembly moves the piercing element back to the retracted position. The diaphragm is sufficiently resilient to close the hole, caused by the piercing element, and to prevent blood from flowing therethrough upon retraction of the piercing element therethrough.

In another aspect of the present invention, a method for withdrawing blood from an appendage includes the steps of seating the appendage against the platform over the recess, and piercing the appendage by engaging the operating means to operably move the piercing means from the retracted position to the extended appendage piercing position. Furthermore, the method includes the step of operating the suction device to facilitate withdrawal of blood from the appendage and transport of the blood specimen to the storage container.

BRIEF DESCRIPTION OF THE DRAWING

The assembly of the present invention has other objects and features of advantage which will be more readily apparent from the following description of the Best Mode of Carrying Out the Invention and the appended claims, when taken in conjunction with the accompanying drawing, in which:

THE BEST MODE FOR CARRYING OUT THE INVENTION

Reference will now be made in detail to the preferred embodiments of the invention. While the present invention has been described with reference to a specific embodiment, the description is illustrative of the invention and is not to be construed as limiting the invention. Various modifications to the present invention can be made to the preferred embodiment by those skilled in the art without departing from the true spirit and scope of the invention, as defined by the appended claims.

Figure 1:
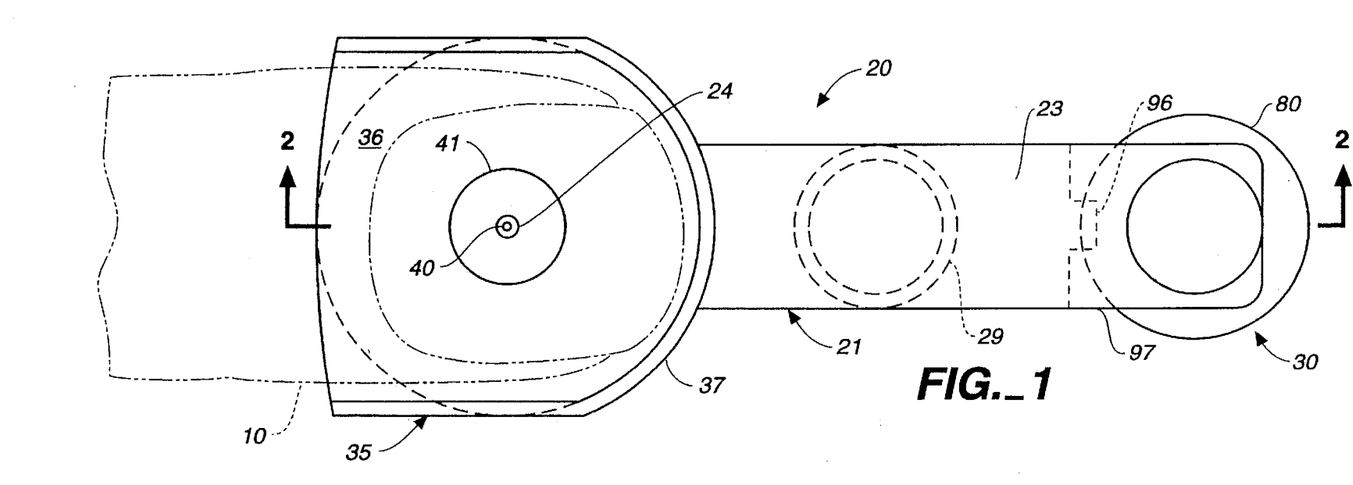
FIG. 1 is top plan view of the self-contained blood withdrawal apparatus constructed in accordance with the present invention.
Figure 2:
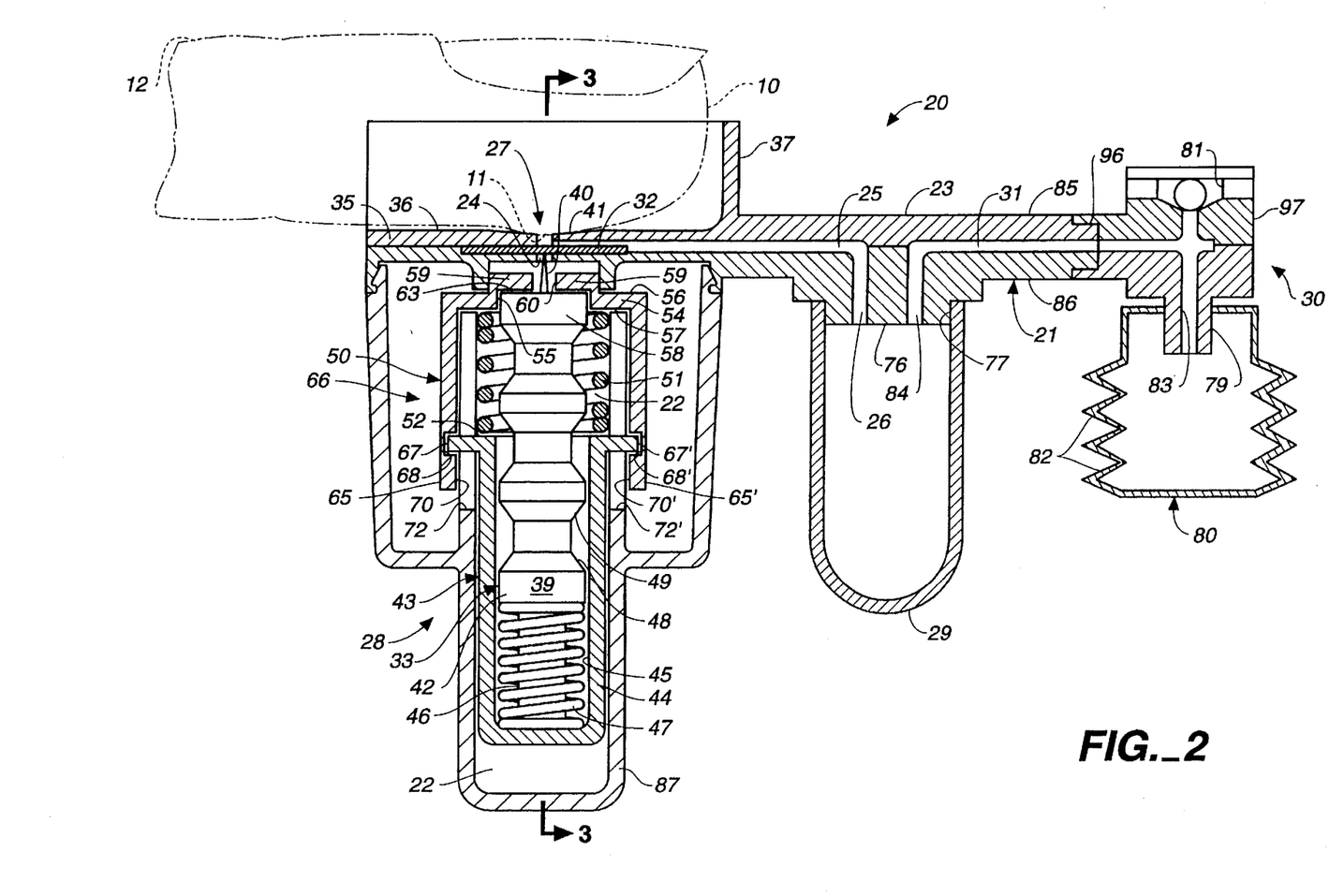
FIG. 2 is a side elevation view, in cross section, of the apparatus of the present invention, taken substantially along the plane 2—2 of FIG. 1.

Attention is now directed to FIGS. 1 and 2, where the subject blood withdrawal apparatus, generally designated 20, is illustrated. In accordance with the present invention, the apparatus 20 provides a self-contained blood withdrawal unit for an appendage which facilitates blood removal and storage, and is, further, disposable, safe and easy to use. Blood withdrawal apparatus 20 comprises, briefly, a base portion 21 defining a cavity 22 and including an upper surface 23 having an opening 24 into the cavity. The base portion is formed with a first passageway 25 which extends from the opening 24 and terminates at an entry port 26. An appendage piercing mechanism, generally designated 27, is formed for drawing blood from an appendage 10. The piercing mechanism is disposed in the cavity and is movable between a retracted position (FIGS. 3A and 3C) and an extended appendage piercing position (FIG. 3B). An operating mechanism or assembly, generally designated 28 is operably coupled to piercing mechanism 27 for movement thereof from the retracted position to the extended position. A storage container, generally designated 29, stores the withdrawn blood and is coupled to base portion 21. The storage container communicates with opening 24 through first passageway 25. A suction mechanism, generally designated 30, facilitates withdrawal of the blood from the appendage. The suction mechanism is removably coupled to base portion 21 through connector 96, and communicates with opening 24 through a second passageway 31, container 29 and first passageway 25.

Further, piercing mechanism 27 may include a resilient, fluid impermeable diaphragm, generally designated 32 (FIGS. 1–3), which is positioned in cavity opening 24 in a manner preventing the drawn blood from flowing through the opening and into cavity 22. A piercing element 33 is movably disposed in the cavity which cooperates with operating assembly 28 to move the piercing element from the retracted position, out of contact with diaphragm 32, to the piercing position. In the piercing position, piercing element 33 extends through a hole 34 (FIG. 3B) in the diaphragm caused by the piercing element to pierce the skin proximate the cavity opening. Once the operating assembly moves the piercing element back to the retracted position, diaphragm 32, being sufficiently resilient, closes or self-seals the hole to prevent blood from flowing therethrough.

Accordingly, the blood will be urged towards first passageway 25 and into storage container 29 when suction mechanism 30 is operated.

The elongated base portion 21 includes an appendage platform 35 is disposed at one end thereof. Preferably, upper surface 23 of base 22 has a platform upper surface portion 36, which is substantially planar in order to provide a support against which an appendage 10 may seat. Upstanding from a substantial portion of the platform perimeter is an upstanding wall or positioning means 37 formed to assist the proper positioning of appendage 10 when seated on the platform upper surface 36. Hence, when a finger tip of appendage 10 (FIG. 2) is supported by platform 35, upstanding wall 37 aligns the finger relative blood withdrawal apparatus 20. It will be appreciated, however, that although upstanding wall 37 is primarily designed to align a finger-shaped appendage 10 for withdrawal of blood therefrom, the present invention may easily be adapted to other appendages as well.

Cavity opening 24, provided by platform upper surface 36, is formed to slidably receive a skin piercing needle or lancet 40 of piercing mechanism 27 therethrough for piercing of the appendage. Surface 36 further may be formed with a recess 41 (FIG. 2) concentrically surrounding and tapered inwardly toward opening 24 to enhance sealing of appendage 10 over opening 24 during blood withdrawal. All of surface 36, of course, may be slightly concave or convex to facilitate positioning of appendage 10, depending on its particular use.

Appendage 10 must be positioned directly over cavity opening 24. As best shown in FIGS. 1 and 2, when appendage 10 is seated against the platform surface 36, and a nominal amount of pressure is applied to hold appendage 10 against platform surface 36, recess 41 and cavity opening 24 will be substantially sealed by the appendage. Moreover, a protuberant portion 11 of appendage 10 bulges into cavity opening 24 (FIG. 2) which increases the firmness at the area targeted for piercing. This facilitates accurate piercing of the skin by piercing element 33.

Figure 3A:
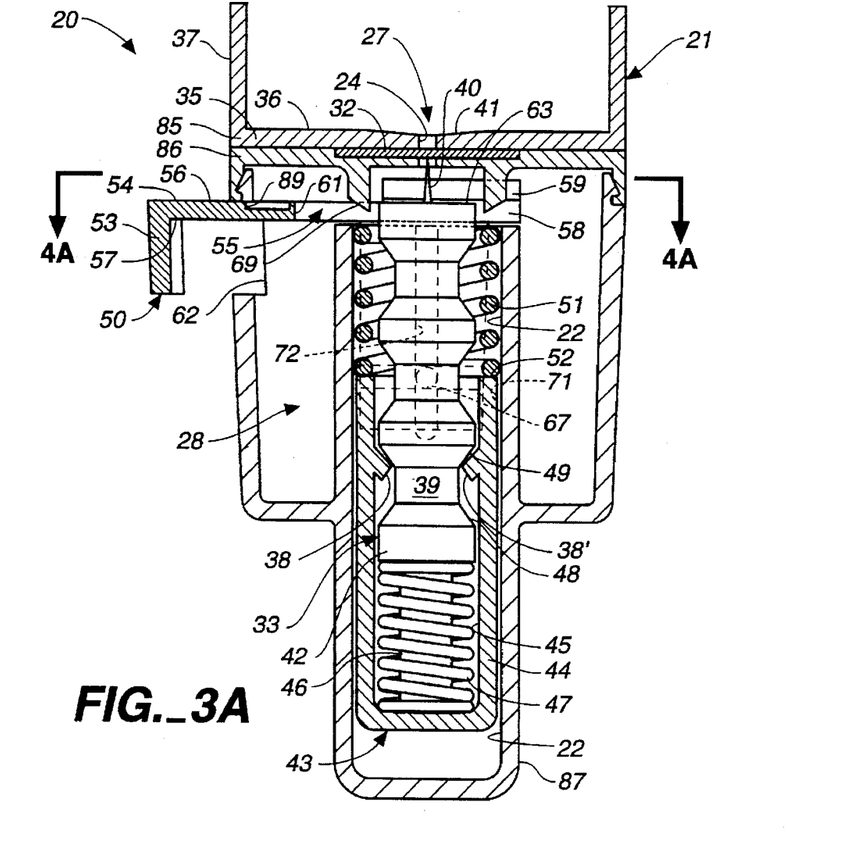
FIGS. 3A–3C are a series of front elevation views, in cross section, of an operation assembly and a piercing mechanism of the self-contained blood withdrawal apparatus, with components in moved positions and taken substantially along the plane 3—3 of FIG. 2.
Figure 3B:
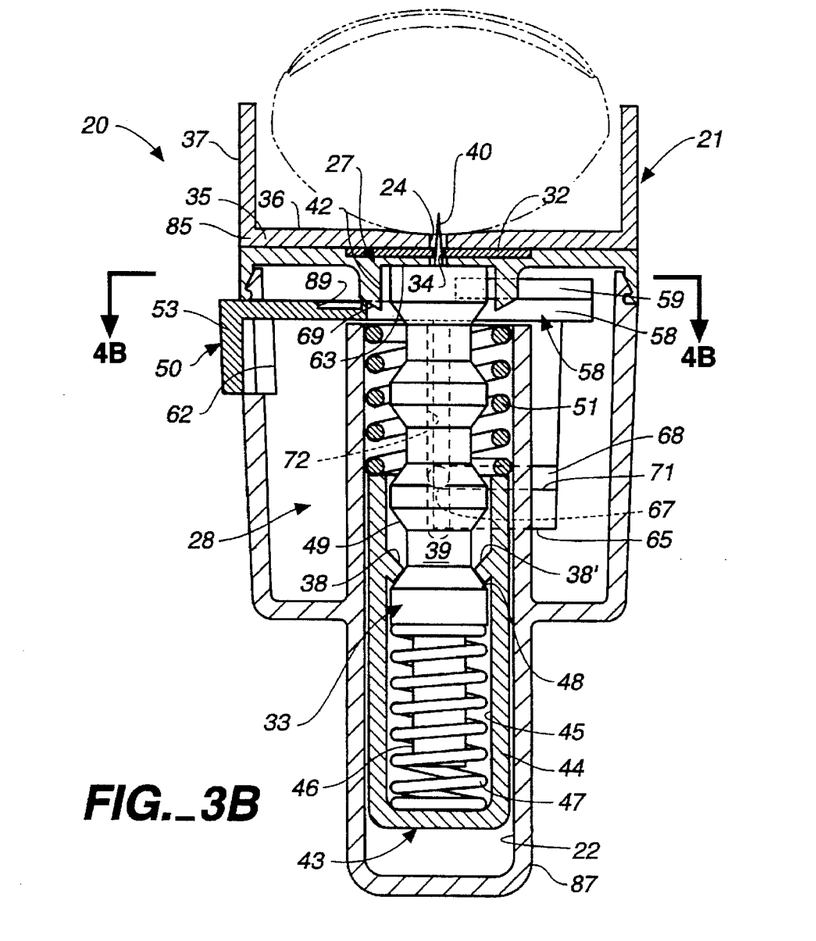
Figure 3C:
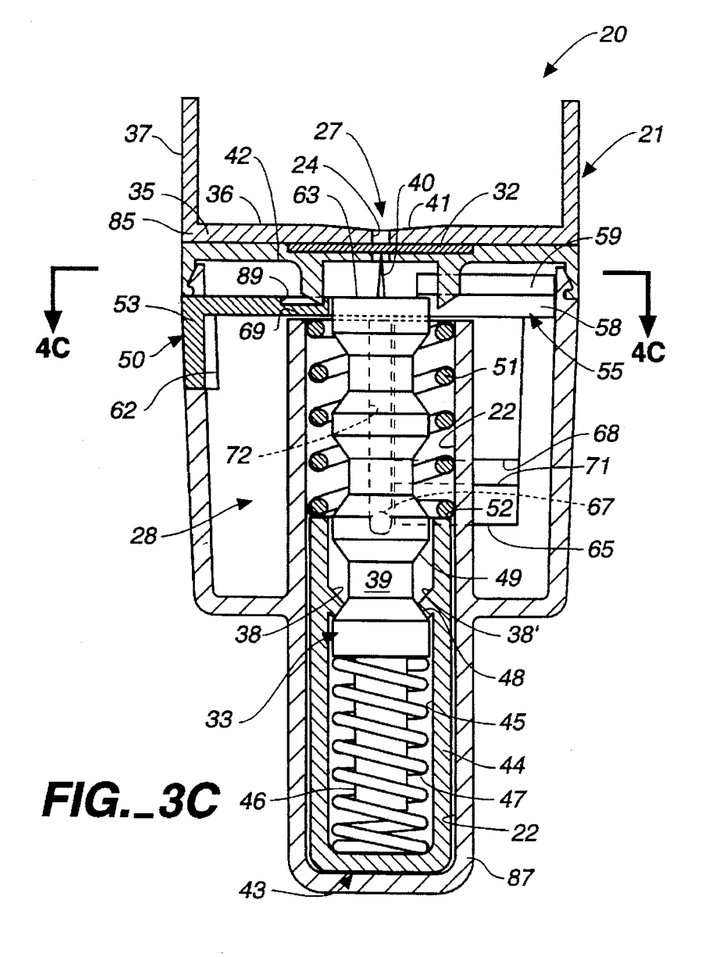

As best viewed in FIGS. 2 and 3, diaphragm 32 is positioned and seated in cavity opening 24 in a manner preventing withdrawn blood from entering cavity 22 through opening 24. Once skin piercing needle or lancet 40 of piercing element 33, to be discussed in greater detail below, has been moved to the piercing position to pierce the diaphragm (and appendage 10 as shown in FIG. 3B), upon withdrawal of needle 40 back to the retracted position, the hole in diaphragm 32 caused by needle 40 must be closed so that withdrawn blood from appendage 10 will not flow into cavity 22. Accordingly, diaphragm 32, preferably rubber or the like, must be sufficiently resilient to substantially self-seal hole 34 upon withdrawal of needle 40 therefrom. It will be understood that the term "self-seal" means that the diaphragm will close hole 34 without additional aid so that the diaphragm will once again be substantially impermeable to the withdrawn blood.

Since diaphragm 32 self-seals hole 34, the blood drawn will be directed through a first passageway 25, which is in open communication with cavity opening 24 above diaphragm 32 (FIG. 2). Upon operation of suction mechanism 30, a vacuum is created throughout storage mechanism 29 and passageways 25, 31 which draws the blood through first passageway 25 and into storage or specimen container 29 for deposition.

Figure 4A:
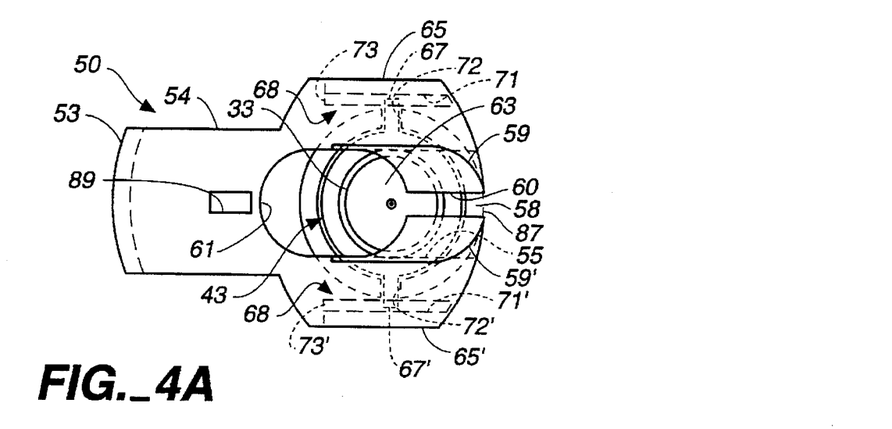
FIGS. 4A–4C are a series of top plan views, in cross section, of the self-contained blood withdrawal apparatus, taken substantially along the plane 4—4 of FIGS. 3A–3C, respectively, and illustrating the interengagement between a button mechanism of the operation assembly and a piston member of the piercing mechanism.
Figure 4B:
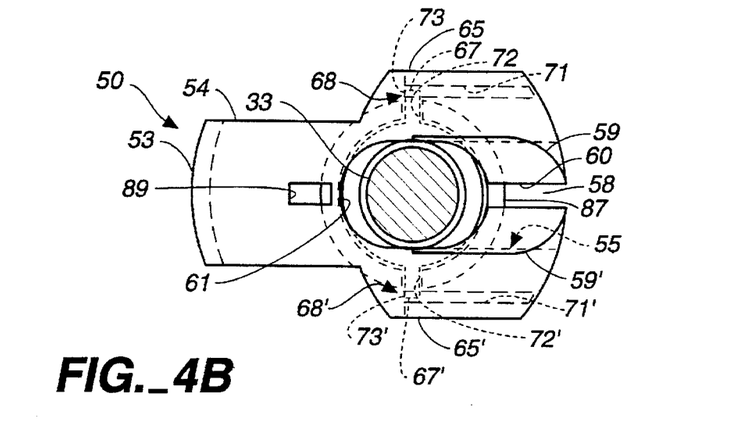

Turning to FIGS. 3A–3C, 4A–4C and 5, the construction and operation of piercing mechanism 27 will now be described in more detail. Piercing mechanism 27 includes a piercing element 33 comprised of an elongated piston member 42 and skin piercing needle or lancet 40 mounted thereatop which is formed to efficiently pierce the skin of appendage 10. Piercing element 33 is reciprocally disposed in retraction cavity 22, in an upright position, so that the lancet 40 pierces appendage 10 substantially perpendicular to the platform surface 36 or diaphragm 32. As mentioned, the piercing element is mounted for sliding movement in retraction cavity 22, relative the base portion, from a normally retracted position (FIGS. 3A, 4A and 3C, 4C) to a piercing position (FIGS. 3B and 4B). More particularly and in accordance with the present invention, operating assembly 28 moves piercing element 33 from: (1) the normally retracted position (FIGS. 3A and 4A), out of contact with diaphragm 32; to (2) the piercing position (FIGS. 3B and 4B), extending through hole 34 in diaphragm caused by piercing needle to pierce the skin of appendage 10 proximate cavity opening 24; and back to (3) the retracted position (FIGS. 3C and 4C), so that the withdrawn blood can be stored in specimen container 29.

In the retracted position, upon which piercing element 33 is situated both before and after movement thereof to the piercing position, no portion of the needle 40 protrudes above the diaphragm 32. Such disposition of piercing element 33 prevents accidental stabbings during periods of non-use and preparation for use of the apparatus 20.

Operating assembly 28 includes a lancet holding assembly 43 movably disposed in cavity 22 which is formed to support the piercing element relative to base portion 21. However, the holding assembly is movable to permit slidable movement of the piercing element, relative to the holding assembly. In the retained condition, piercing element 33 is prevented from moving to the piercing position, while in the actuated condition, piercing element 33 is permitted to move to the piercing position. Moreover, when the piercing element is in the actuated condition, it may be moved back to the retracted position by the holding assembly such that needle or lancet 40 is withdrawn from piercing engagement with diaphragm 32 and the patient's finger.

Lancet holding assembly 43 is preferably provided by a cup-shaped support member 44 axially received in retraction cavity 22 of base portion 21. Support member 44 in turn is formed with a piston receiving bore 45 coaxially aligned with retraction cavity 22 and formed and dimensioned to telescopically receive lancet piston member 42 therein for movement and support of the piercing element. Holding assembly 43 includes an advancement spring element 47 (FIGS. 3 and 5) which biases piercing element 33 toward the actuated condition. Upward motion-inducing spring 47 is preferably provided by a compression spring positioned in receiving bore 45 having one end seated against the cup-shaped support 44 and an opposite end abutting the piston member 42. Piercing element 33 includes a guiding post 46 extending downwardly from a lower distal end of piston member 42 into spring 47, which is formed to align piston member 42 during telescopic movement thereof from the retained condition to the actuated condition.

In addition, cup-shaped support 44 includes a pair of opposing tang members 38, 38' which limit the reciprocal movement of piercing element 33 in bore 45 relative holding assembly 43 between the retained condition and the actuated condition. FIGS. 3A–3C show that tangs 38, 38' extend downward and inward from an interior wall forming receiving bore 45. Piston member 42 provides a neck portion 39 between an upwardly facing ledge portion 48 and a downwardly facing ledge portion 49. Accordingly, neck portion 39 is dimensioned to slidably reciprocate between tangs 38, 38' until downwardly facing ledge portion 49 seats against tangs 38, 38' (FIG. 3A) to align piercing element 33 in the retained condition, and until upwardly facing ledge portion 48 seats against ends of tangs 38, 38' (FIGS. 3B and 3C) to align piercing element 33 in the actuated condition.

Figure 4C:
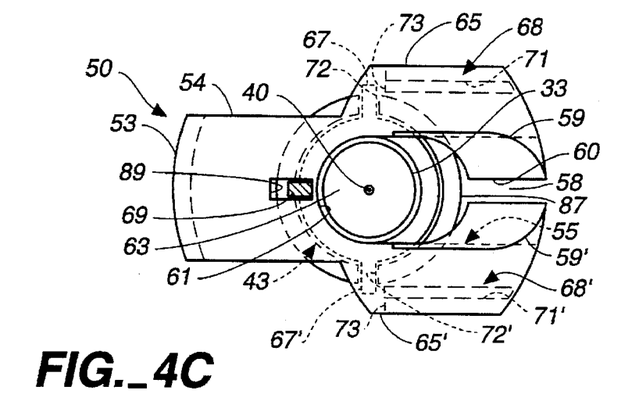

Operating assembly 28 further includes a button retention-retraction mechanism, generally designated 50, which retains and releases holding assembly 43 for movement from a suspended position (FIGS. 3A, 4A and 3B, 4B) to a released position (FIGS. 3C, 4C). The button mechanism also retracts the piercing element from the piercing position back to the retracted position, while the piercing element remains in the actuated condition (FIGS. 3C, 4C), relative the holding assembly.

A return spring element 51 (FIGS. 3 and 5) is positioned in cavity 22 between button mechanism 50 and holding assembly 43 which biases the holding assembly toward the released position. Return spring 51 is also preferably provided by a compression spring positioned in retraction cavity 22 having one end abutting button mechanism 50 and an opposite end seated against a top edge portion 52 of cup support member 44. Accordingly, advancement spring 47 urges piercing element 33 upwardly toward the actuated condition, relative holding assembly 43, while return spring 51 urges the holding assembly downwardly toward the released position, relative base portion 21.

In accordance with the present invention, button mechanism 50 operably interengages and coordinates movement between piercing element 33, holding assembly 43 and base portion 21. Button mechanism 50 is mounted to base portion 21 for movement from a first position to a third position (FIGS. 3A, 4A to 3C, 4C). In the first position (FIGS. 3A, 4A), button mechanism 50 enables: (1) piercing element 33 to be retained in the retracted position, relative to base portion 21; (2) the piercing element to be retained in the retained condition, relative holding assembly 43; and (3) the holding assembly to be retained in the suspended position, relative the base portion. In the second position (FIGS. 3B, 4B), button mechanism 50 enables: (1) piercing element 33 to move to the piercing position, relative base portion 21; and (2) the piercing element to move to the actuated condition, relative holding assembly 43; while (3) the holding assembly is retained in the suspended position, relative the base portion. Finally, in the third position (FIGS. 3C, 4C), button mechanism 50 enables: (1) holding assembly 43 to move to the released position, relative base portion 21; and (2) piercing element 33 to move back to the retracted position, relative the base portion; while (3) the piercing element is retained in the actuated condition, relative the holding assembly.

Figures 5, 6, 10:
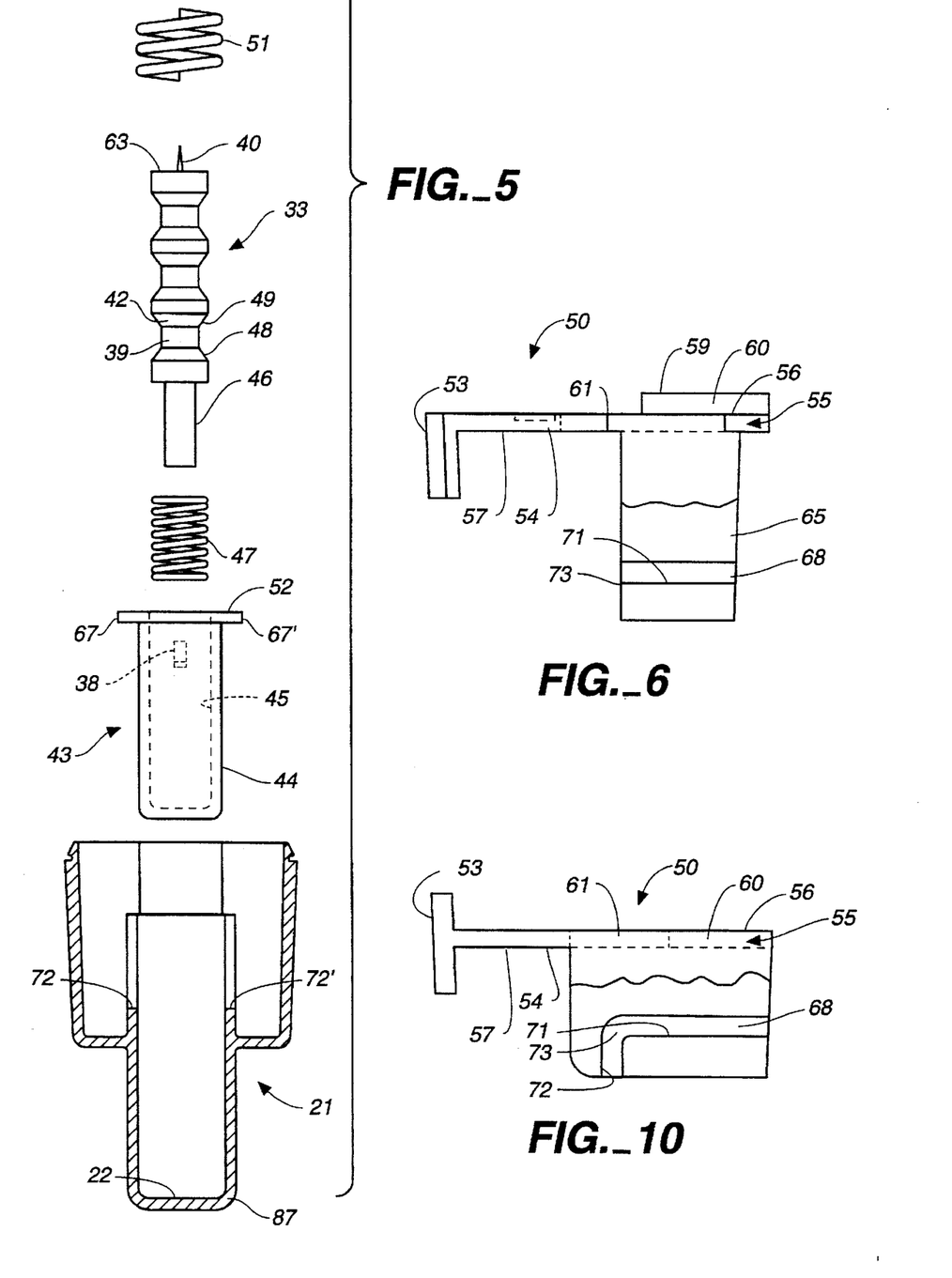
FIG. 5 is an exploded, side elevation view, in partial cross-section, of the operation assembly and the piercing mechanism of the self-contained blood withdrawal apparatus of FIG. 2.
FIG. 6 is a front elevation view, partially broken away, of the button mechanism of the operation assembly of the present invention.
FIG. 10 is a front elevation view, partially broken away, of an alternative embodiment of the button mechanism.

As best viewed in FIGS. 4 and 6, button mechanism 50 includes a manually engagable knob member 53 coupled to a retaining wall 54 extending outward therefrom. The retaining wall provides an actuating slot 55 extending therethrough from a top surface 56 to a bottom surface 57 which is formed to slidably receive piston member 42 therein. Upstanding from retaining wall 54 proximate a mouth portion 58 of actuating slot 55 is a pair of opposing ridges 59, 59' which define a needle receiving region 60. FIG. 2 best illustrates that needle receiving region 60 is positioned just above a mouth portion 58 of actuating slot 55 and is formed to slidably receive the needle of piercing element 33 therein.

The width of the needle receiving region, however, is substantially narrower than the width of actuating slot 55 so that an upward facing shoulder portion 63 of piston member 42 cannot extend therethrough (FIGS. 2 and 4A). The advancement spring 47, accordingly, which biases piercing element 33 toward the actuated condition, urges shoulder portion 63 against a bottom surface of opposing ridges 59, 59'. Piercing element 33 will thus be prevented from moving to the actuated condition as needle 40 slides longitudinally along the length of needle receiving portion 60.

During manual engagement of the button mechanism knob 53 in the direction of arrow 64 (FIGS. 3 and 4) from the first position (FIG. 4A) to just before the second position (FIG. 4B), the needle 40 is permitted to move longitudinally along needle receiving region 60 while shoulder portion 63 of piston member 42 is permitted to slide longitudinally along actuating slot 55. As mentioned, however, the piercing element 33 is not permitted to move perpendicular to retaining wall 54 toward the actuated condition until button mechanism is moved to the second position. In this position (FIGS. 3B and 4B), the needle 40 is moved past the needle receiving region 60 which terminates at a shoulder receiving region 61 of actuating slot 55 formed to receive the transverse cross-sectional dimension of piston member 33 perpendicularly therethrough. The piston member, thus, is permitted to extend through actuating slot 55 (via advancement spring 47) so that piercing element 33 can move to the actuated condition (FIGS. 3B, 4B).

Once the button mechanism has moved to the second position and advancement spring 47, supported by holding assembly 43, has urged piercing element upwardly toward the actuating condition, the holding assembly remains in the suspended position relative base portion 21. Importantly, when button mechanism 50 is in the second position, piercing element is moved from the retracted position to the piercing position, relative base portion 21, until downward facing ledge portion 49 seats against tangs 38, 38' to limit movement thereof. Skin piercing needle then extends through cavity opening 24 and through resilient diaphragm 32 to pierce appendage 10.

As best viewed in FIG. 6, button mechanism 50 includes a pair of aligning flanges 65, 65' extending downwardly from retaining wall 54 which are spaced-apart by a distance sufficient to slidably receive the upper portion of cup-shaped support member 44 therebetween. Operating assembly 28 further includes a track mechanism, generally designated 66, positioned between the button mechanism and the holding assembly to guide the movement of the holding assembly between the aligning flanges of the button mechanism. Moreover, this, in turn, guides movement of the holding assembly from the suspended portion to the released portion as the button mechanism moves from the first position to the third position.

Track mechanism 66 is preferably provided by a pair of opposing guide pins 67, 67' (FIGS. 2 and 4), extending radially outwardly from the outer perimeter of cup-shaped support member 44, which slidably engage corresponding guide grooves 68, 68' dimensioned to slidably receive guide pins 67, 67' therein. Each guide groove is comprised of a first substantially horizontal path 71 (FIGS. 3 and 6) intersecting a second substantially vertical path 72 at an elbow portion 73. In the preferred form, first path 71 extends along interior surface 70 of aligning flange 65 (FIG. 6), while the second path is provided as release slot 72 extending along base portion 21 which forms retraction cavity 22 (FIG. 3).

In accordance with the present invention, as button mechanism 50 is manually moved and operated from the first position (FIGS. 3A, 4A) to the second position (FIGS.

3B, 4B), in the direction of arrow 64, guide pins 67, 67' slidably engage first path 71, 71', respectively, which suspend cup-shaped support member 44 therefrom in retraction cavity and permit piercing element to move to the piercing position (FIG. 3B), relative base portion 21. Once the button mechanism is positioned at the second position, proximate elbow portion 73, further manual movement of the button mechanism toward the third position, in the direction of arrow 64, moves guide pins 67, 67' into elbow portion 73, 73' so that the guide pins move past first paths 71, 71', out of suspended contact therewith, and can enter the second paths 72, 72', respectively. As shown in FIGS. 3C and 4C, second paths 72, 72' align with first paths 71, 71' at elbow portions 73, 73'. Upon this occurrence, return spring 51 urges the top edge portion 52 of cup support member 44 downwardly which pushes holding assembly 43 toward the released position (FIG. 3C). In response, cup-shaped support member 44 is forced into retraction cavity 22 which retracts the piercing element, relative the base portion, from piercing engagement with appendage 10 and diaphragm 32.

To prevent button mechanism 50 from inadvertently moving back to the first or second position once manually moved to the third position, a retention knob 69, extending downward from platform 35, is provided which interengages a depression 89 formed in top surface 56 of retaining wall 54 to prevent movement therebetween. FIGS. 3A–3C illustrate that depression 89 is formed to retainably, receive knob 69 therein to lock button mechanism 50 relative platform 35. The depression is properly aligned along top surface 56 at an orientation where interengagement occurs when button mechanism 50 is moved to the third position (FIG. 3C) and a ramped portion of knob 69 moves over top surface 56 and into depression 89. Further, base portion 21 includes a socket 62 formed to receive knob member 53 therein so that when button mechanism 50 is moved to the third position (FIG. 3C), the knob member is positioned in socket 62 to reduce inadvertent removal of button mechanism from the third position.

In an alternative embodiment of button mechanism 50, guide grooves 68, 68' may be fully integrated into respective aligning flanges 65, 65'. As shown in FIG. 10, interior surface 70 of flange 65 forms both first horizontal path 71 and second vertical path 72 which intersect at elbow portion 73. Similar to the preferred form, once the button mechanism is positioned at the second position, proximate elbow portion 73, further manual movement of the button mechanism toward the third position move guide pin 67 into elbow portion 73 so that the guide pin moves past first path 71 and can enter second path 72. Return spring 51 then urges holding assembly 43 downwardly toward the released position (FIG. 3C).

This alternative form of button mechanism 50 also requires base portion 21 to include a pair of opposing release slots (the second vertical path slots 72, 72' in base portion 21 in FIG. 5) which align with second vertical paths 72, 72', respectively in aligning flanges 65, 65', when the button mechanism is moved to the third position. Upon alignment, the release slots permit guide pins 67, 67' to move along second path 72, 72', respectively.

It will be understood that while piercing element 33 is moved back to the retracted position, relative base portion 21, the piercing element remains in the actuated condition, relative holding assembly 43. Thus, it is the movement of the holding assembly to the released condition which moves the piercing element to the retracted position, relative the base portion. Further, the shoulder receiving region 61 of actuating slot 55 must be sufficiently wide, laterally, to permit piston member 42 to unobstructively reciprocate therethrough so that piercing element 33 can retract back into cavity 22.

In accordance with the present invention, storage container 29 is preferably releasably coupled to base portion 21 for receipt of the blood specimen therein. Unlike the prior art blood lancet assemblies which are not self-contained, the present invention includes a means for collecting and storing the blood specimens. Specimen tubes 29 are well known in the medical profession and may include a variety of volume capacities and lengths.

Moreover, storage container 29 may be pre-filled with predetermined amounts of anti-coagulants, or other blood specimen influencing chemicals or additives, such as buffers, pH indicators, enzyme inhibitors, or the like. Direct contact with these chemicals or additives can prevent clotting and reduce potential contamination of the specimen during handling.

Extending downward from the base portion bottom surface, preferably adjacent button mechanism 50, is a storage container mounting column 76 upon which storage container 75 is releasably mounted. Column 76 is formed to frictionally engage and seal against the container inner perimeter 77, defining the container opening, so that container 29 may be releasably retained on base portion 21. Accordingly, the exterior surface of container mounting column 76 is tapered inwardly as it extends downward from the base portion bottom surface. This taper substantially conforms to the taper of the storage container interior perimeter 77 so that upon sliding engagement therebetween, a seal sufficient to hold a slight vacuum, is formed. Moreover, storage container 29 is positioned onto mounting column 76 until the top peripheral lip portion 78 of storage container 29 abuts the base portion bottom surface, as shown in FIG. 2. This abutment against the bottom surface limits the positioning of storage container 29 with respect to column 76. Potentially, this structure also minimizes or eliminates the difficulties encountered if the storage container 29 were positioned too far onto container mounting column 76.

Although storage containers 29 may include a variety of volume capacities and lengths, as well as material composites, it is preferable that the storage container opening perimeters 77 be substantially similar when used in conjunction with a particular withdrawal apparatus 20. It will be appreciated, however, that container mounting column 76 can be easily modified to accept a different diameter storage container opening perimeter 77.

A suction mechanism 30 is removably mounted to elongated base portion 21 through connector 96 on the end opposite to that on which platform 35 is disposed. Suction mechanism 30 generates a continuous vacuum, when operated, which facilitates the withdrawal of the blood specimen and its transport from opening 24 to storage container 75. As shown in FIG. 2, suction mechanism 30 preferably comprises a bellow-pump 80 and a one-way valve 81 formed to control the direction of the pumped air. Bellow-pump 80 is a standard pump mechanism commonly known in which the individual bellows 82 of the pump are flexible members which define bellow cavity 22. Flexible bellows 82 permit compression of the pump 80 which reduces the volume of bellow cavity 22 and displaces the air contained therein.

Moreover, pump 80 is preferably removable from a pump base 97 of suction mechanism 30 and reusable. Using a mounting technique similar to storage container 29, pump 80 is releasably mounted to a pump mounting column 79 which extends downward from the base portion bottom surface. Pump mounting column 79 is dimensioned to snugly insert into a bellows opening 24 to retain it thereon. Upon insertion, bellow neck 83 slidably engages pump mounting column 79, forming a seal therebetween, which must be sufficient to sustain the vacuum generated when the suction mechanism 30 is operated.

In the preferred form, one-way valve 81 is integrated into the pump base upper surface opposite bellow-pump 80. Valve 81, also commonly known, provides a means for a one direction removal of air from bellow cavity 22 when bellows 82 are collapsed. Thus, when the compressed bellows 82 are disengaged, allowing flexible bellows 82 to expand, one-way valve 81 does not permit air outside apparatus 20 to re-enter the bellow cavity 22. Accordingly, a continuous vacuum is generated within apparatus 20.

A second passageway 31 extends through base portion 21 and pump base 97 to provide a communication pathway between suction mechanism 30 and cavity opening 24. Preferably, second passageway 31 extends through container mounting column 76, as viewed in FIG. 2, and terminates at a suction communication port 84 at storage container 29. Second passageway 31, further, communicates with valve 81, as well as, bellow pump 80. Accordingly, when a vacuum is created by suction mechanism 30, the vacuum is communicated to opening 24 a first passageway 25, storage container 29, and second passageway 31.

Before operation of blood withdrawal apparatus 20 of the present invention, bellow-pump 80 and storage container 29 must be installed onto base portion 21. Subsequently, to operate piercing mechanism 27, the medical technician positions the patient's appendage over opening 24 and seats it against the platform upper surface 36, as shown in FIGS. 1 and 2. A slight pressure is applied to a top side 12 of appendage 10 to create the protuberance 11 into opening 24. The technician then positions their finger on manually engagable knob member 53 of button mechanism and pushes it in from the first position to the third position in one swift and continuous stroke. Ultimately, this moves piercing element 33 from the retracted position (FIG. 3A) to the piercing position (FIG. 3B) and back to the retracted position (FIG. 3C).

As above-indicated, upon withdrawal of skin piercing needle 40 from diaphragm 32, the hole in diaphragm caused by needle 40 self seals so as to be impermeable to blood. After appendage 10 has been pierced by needle 40 to draw blood and while still maintaining a seal over opening 24, the technician will operate suction mechanism 30. As bellow-pump portion 80 is compressed and the bellows 82 are collapsed, the air contained in bellow cavity 22 is forced out through one-way valve 81. Upon return of bellows 82 to their normal position, a vacuum is created throughout the first and second passageways 25 and 31, respectively, and within storage container 29. After a few similar repetitions, a sufficient suction or vacuum is created to withdraw blood from appendage 10. The withdrawn blood passes through first passageway 25 and out blood entry port 26 where it is deposited in storage container 29. After the proper amount of blood has been withdrawn, typically 750 microliters, appendage 10 may be separated from cavity opening 24 which breaks the seal created therebetween. Subsequently, storage container 29 containing the blood specimen, and bellow-pump 80 are removed from their respective mounting columns 76 and 79, and base portion 21 is discarded.

It will be appreciated that suction mechanism 30 may be provided by a mechanical vacuum pump or the like (not shown) removably coupled to connector 96. Such a vacuum source must provide a continuous vacuum, and be capable of mounting to connector 96 in a manner forming a proper seal therewith for suction purposes.

As is apparent from the discussion of the blood withdrawing apparatus 20 of the present invention, the method for withdrawing blood from appendage 10 may be accomplished by seating appendage 10 against platform 35 and over cavity opening 24. Appendage 10 is then pierced by needle 40 which draws blood. Subsequently, suction mechanism 30 is operated to assist the withdrawal of blood and enable its transport to specimen or storage container 29.

Preferably, as shown in FIG. 2, base portion 21 is provided by an upper base member 85 forming platform 35 and a lower base member 86 which sandwiches diaphragm 32 therebetween. A lower carriage member 87, coupled to lower base member 86 below platform 35, forms a portion of retraction cavity 22 so that the holding assembly cup-shaped support member 44 can be slidably supported therein. Base portion 21 is preferably provided by an injection molded thermoplastic material such as plastic. Further, skin piercing needle 40 is preferably metallic, but may be composed of ceramic or the like without departing from the true nature and scope of the present invention.

Figure 7:
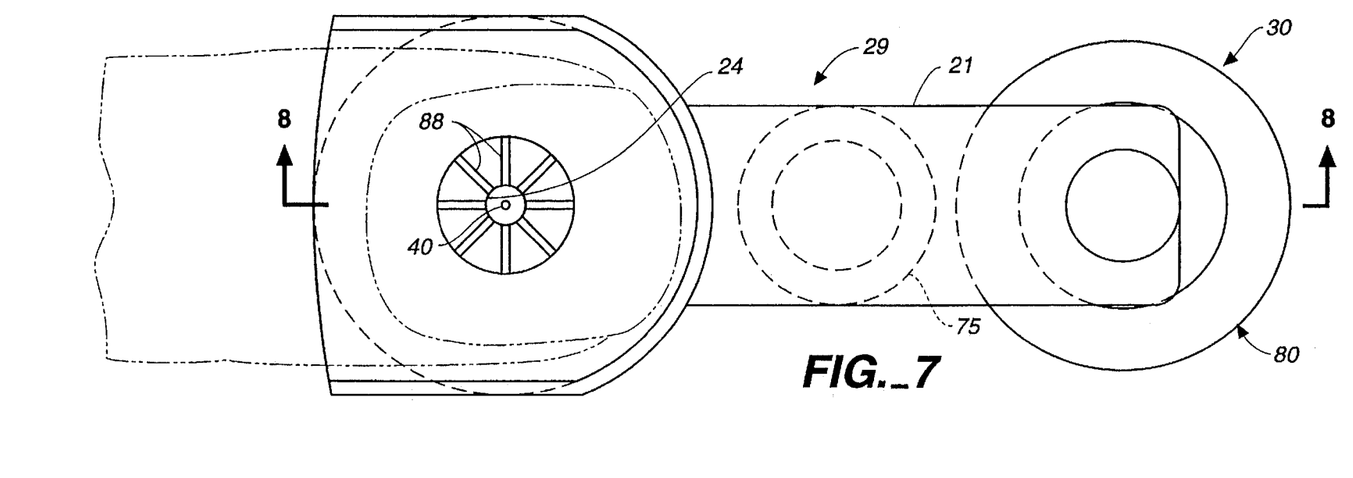
FIG. 7 is top plan view of an alternative embodiment of the self-contained blood withdrawal apparatus constructed in accordance with the present invention and including upstanding support webs.
Figure 8:
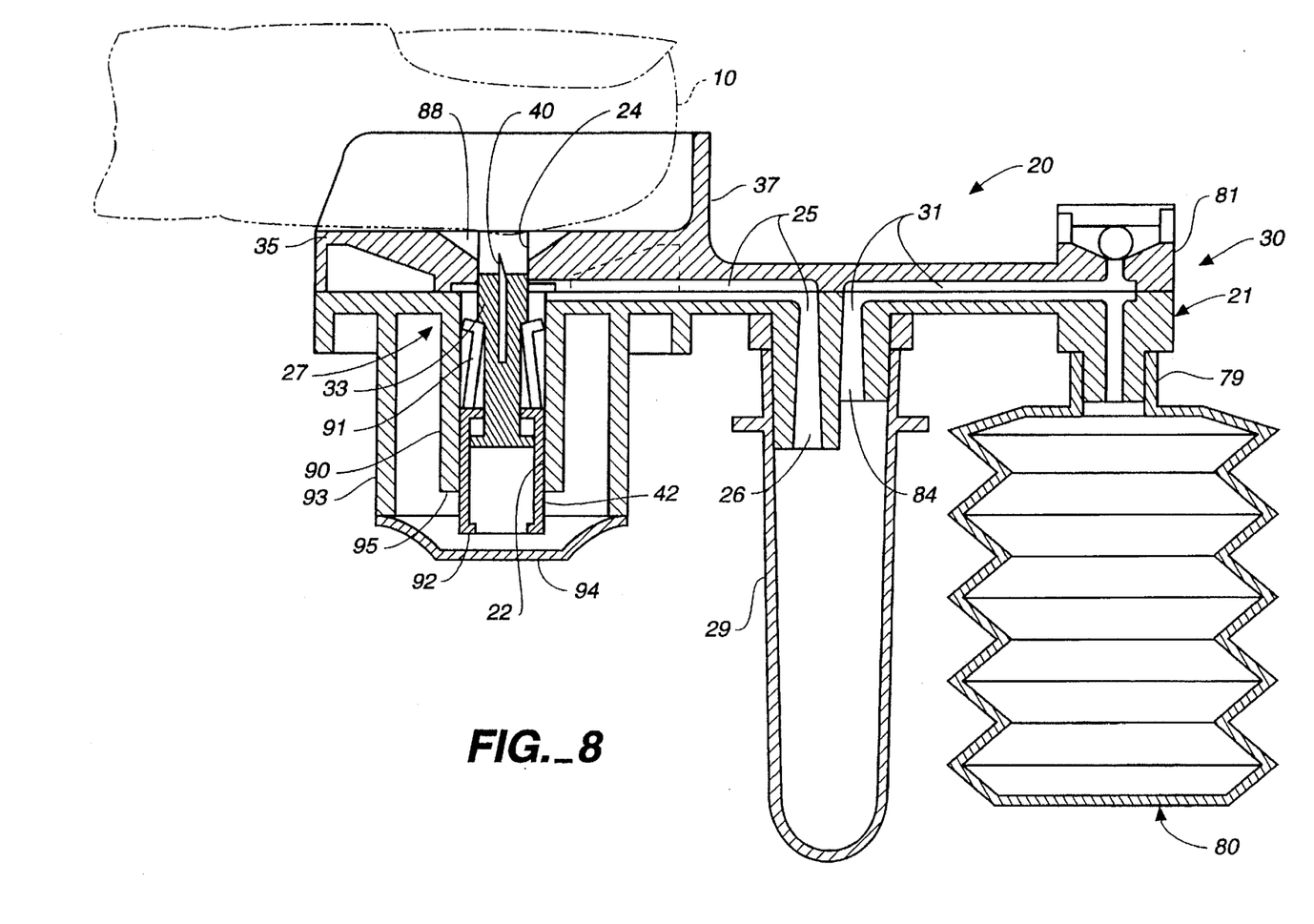
FIG. 8 is a side elevation view, in cross section, of the alternative embodiment of FIG. 7, taken substantially along the plane 8—8 of FIG. 7, and illustrating an alternative piercing mechanism.

In another embodiment of the blood withdrawing apparatus of the present invention, attention is directed to FIGS. 7 and 8 where platform 35 includes a plurality of equally spaced upstanding support webs 88 disposed around and collectively defining cavity opening 24. The depth of retraction cavity 22 should be sufficient to retain the piercing element 33 in the retracted position. Preferably, eight equally spaced webs 88 provide additional support for appendage 10 to seat against, while the passages formed therebetween provide a means which allow the withdrawn blood to pass through. It will be appreciated that more or less webs 88 may be provided without departing from the present invention.

Figure 9:
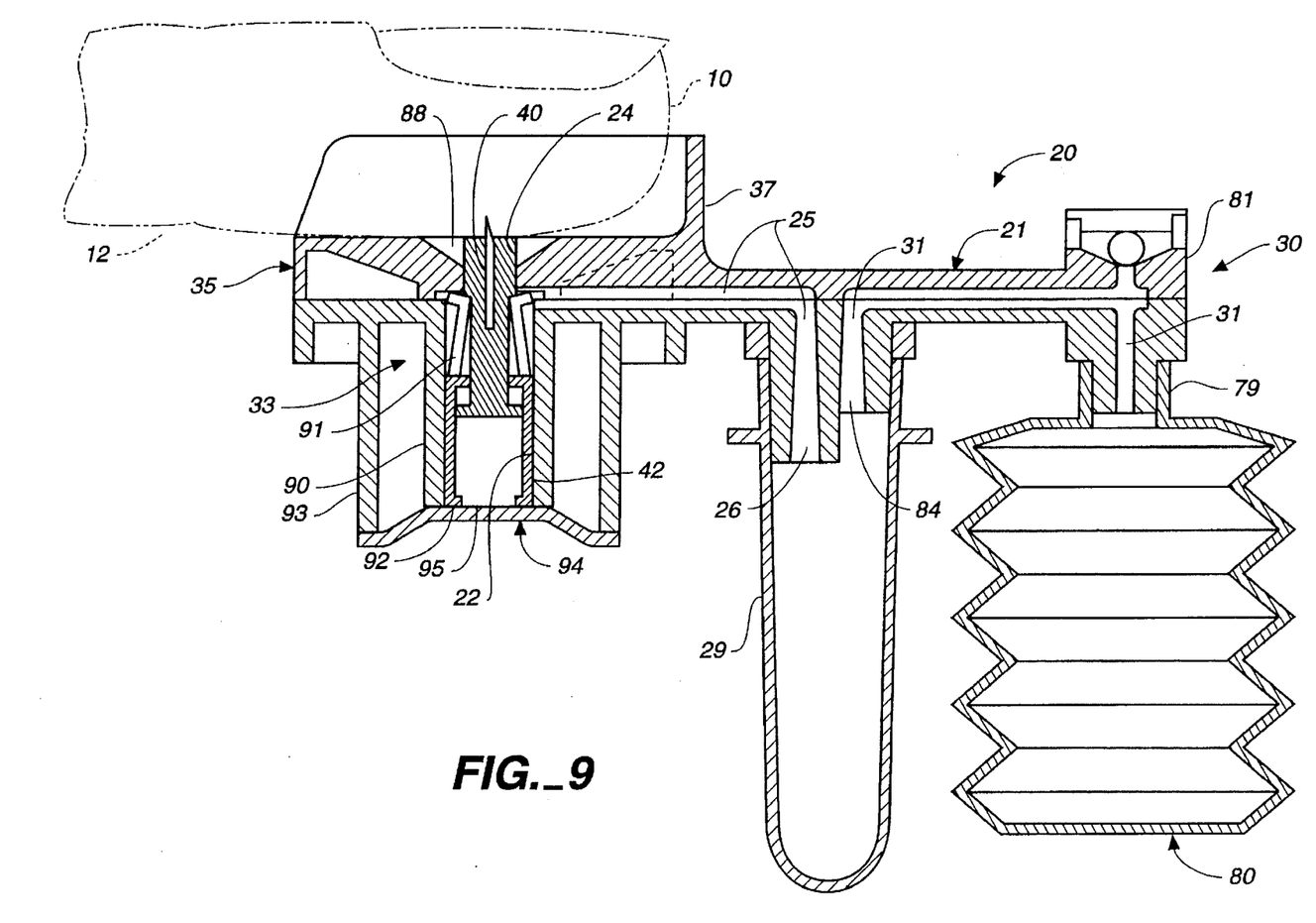
FIG. 9 is an enlarged side elevation view, in cross section, of the apparatus of FIG. 8 illustrating the piercing element manually moved to an appendage piercing position.

FIGS. 7–9 further illustrate an alternative piercing mechanism 27. In this embodiment, base portion 21 provides a tubular piston support guideway 90 which forms retraction cavity 22 and extends downward substantially perpendicular to the platform bottom side. Thus, piercing element 33 slidably engages an inner wall of guideway 90 so that piercing element can reciprocate between the normally biased retracted position (FIG. 8) and the extended appendage piercing position (FIG. 9). The extension of piston member 42 allows skin piercing needle 40 to move smoothly and accurately with respect to the platform 35. Moreover, the engagement between the piston member 42 and guideway 90 guides piercing needle 40 so that the it more accurately pierces appendage 10.

Similar to the previous embodiment, a biasing spring 91 biases piercing element 33 toward a retracted position (FIG. 8) to help prevent accidental stabbings during nonuse. Biasing spring 91 is seated against piston member 42 to urge piercing element away from appendage 10 in a manner where a bottom end portion 92 of piston member 42 protrudes beyond the lower end of piston guideway 90. When biasing spring 91 urges piston member 42 downward, a bottom end portion 92 of piston member 42 protrudes beyond the lower end of the piston guideway 90, as illustrated in FIG. 8. This provides a means for manual displacement of piercing element 33.

A plunger support structure 93 also extends downward from the bottom surface of base portion 21 concentric to piston guideway 90. Plunger support 93 is preferably cylindrical and provides a support structure for a manually engageable, resiliently flexible button member 94 disposed on the end thereof. Button member 94 is operably positioned relative to piston member 42 so that when button 94 is upwardly displaced, it engages the piston bottom end portion 92, urges piston member 42 upward in a direction toward appendage 10. As clearly illustrated in FIG. 9, the piston member travels axially through retraction cavity 22, compressing spring 91, until button member 94 abuts lower distal end 95 of piston support guideway 90. Therefore, piston support guideway 90 also functions as an automatic piston stop, which, hence, limits the travel of needle 40 into appendage 10 (FIG. 9). Subsequently, upon manual disengagement of button member 94, biasing spring 91 urges the piercing element back toward the retracted position.

It will be noted that button member 94 preferably comprises a flexible member, such as a flexible plastic or rubber member affixed to plunger support 93 by an adhesive.

In the alternative embodiment as shown in FIG. 8, blood entry port 26 is positioned at an elevation level lower than that of suction communication port 84. This elevation differential helps prevent the passage of withdrawn blood from entry port 26 into suction communication port 84. Accordingly, the withdrawn blood will only be deposited in storage container 29 and will not pass up into second passageway 31 and bellows pump 80.

What is claimed is:

1. A self-contained blood withdrawal apparatus for an appendage comprising:

a base portion defining a cavity and including an upper surface having an opening into said cavity, said base portion being formed with passageway means extending from said opening;

an appendage piercing mechanism formed for drawing blood from the appendage, said piercing mechanism being disposed in said cavity and movable between a retracted position and an extended appendage piercing position;

an operating mechanism positioned relative to said piercing mechanism for moving said piercing mechanism between the retracted and extended positions;

a storage container for storing withdrawn blood coupled to said base portion and communicating with said opening through said passageway means; and a suction mechanism for facilitating withdrawal of said blood from said appendage, said suction mechanism coupled to said base portion and communicating with said opening through said passageway means.

2. The blood withdrawal apparatus as defined in claim 1 wherein, said appendage piercing mechanism comprises a lancet.

3. The blood withdrawal apparatus as defined in claim 1 wherein, said appendage piercing mechanism includes a spring member biasing said piercing mechanism in a normally retracted position.

4. The blood withdrawal apparatus as defined in claim 3 wherein, said appendage piercing mechanism includes a lancet coupled to said spring member.

5. The blood withdrawal apparatus as defined in claim 1 wherein, said passageway means includes a first passageway portion extending between said opening and said storage container and a second passageway portion extended between said storage container and said suction mechanism.

6. The blood withdrawal apparatus as defined in claim 5 wherein, said base portion includes a container mounting column extending downward from a base bottom surface, and said storage container is removably mounted on said mounting column in a substantially sealed relation thereto.

7. The blood withdrawal apparatus as defined in claim 6 wherein, said first passageway extends through said mounting column and terminates at a blood entry port; and said second passageway extends through said mounting column and terminates at a suction communication port.

8. The blood withdrawal apparatus as defined in claim 7 wherein, said blood entry port is positioned at a level below said suction communication port.

9. The blood withdrawal apparatus as defined in claim 1 wherein, said suction mechanism comprises a pump.

10. The blood withdrawal apparatus as defined in claim 9 wherein, said pump is manually operable.

11. The blood withdrawal apparatus as defined in claim 1 wherein, said suction mean comprises a bellows-type pump including valve mechanism coupled to said passageway portion for controlling the passage of air flowing therethrough.

12. The blood withdrawal apparatus as defined in claim 11 wherein, said valve mechanism comprises a one-way valve.

13. The blood withdrawal apparatus as defined in claim 1 wherein, said suction mechanism is releasably coupled to said base portion.

14. The blood withdrawal apparatus as defined in claim 1 further including, appendage positioning element mounted to said base portion for facilitating positioning of the appendage relative to said opening.

15. The blood withdrawal apparatus as defined in claim 14 wherein, said appendage positioning element comprises a wall member upstanding from the platform upper surface perimeter.

16. The blood withdrawal apparatus as defined in claim 1 wherein, said appendage piercing mechanism includes a resilient, fluid impermeable diaphragm positioned in said cavity opening in a manner preventing said drawn blood from flowing through said opening into said cavity urging said blood to flow through said passageway means, and a piercing element movably disposed in said cavity, and said operating mechanism cooperating with said piercing element to move said piercing element, relative said base, from a retracted position out of contact with said diaphragm, to a piercing position, extending through a hole in said diaphragm caused by said piercing element to pierce the skin proximate said cavity opening, and to move back to said retracted position, said diaphragm being sufficiently resilient to self-seal said hole and prevent blood from flowing therethrough upon retraction of said piercing element therethrough.

17. The blood withdrawal apparatus as defined in claim 16 wherein, said operating mechanism includes a lancet holding assembly movably disposed in said cavity and formed to slidably support said piercing element, relative said holding assembly, between
   (a) a retained condition, preventing said piercing element from moving to said piercing position, and
   (b) an actuated condition, permitting said piercing element to move to said piercing position.

18. The blood withdrawal apparatus as defined in claim 17 wherein, said holding assembly is slidably supported in said cavity, relative said base portion, between
   (a) a suspended position, permitting said piercing element to move to said piercing position upon said piercing element moving to said actuated condition, relative said holding assembly, and
   (b) a released position, withdrawing said piercing element from said piercing position while said piercing element remains in said actuated condition, relative said holding assembly.

19. The blood withdrawal apparatus as defined in claim 18 wherein, said operating assembly includes a button mechanism operably interengaged with said piercing element and said holding assembly for coordinating movement therebetween, said button mechanism moving from:
   (a) a first position enabling
      1) said piercing element to be retained in said retracted position, relative said base portion,
      2) said piercing element to be retained in said retained condition, relative said holding assembly, and
      3) said holding assembly to be retained in said suspended position, relative said base portion; to
   (b) a second position enabling
      1) said piercing element to move to said piercing position, relative said base portion, and
      2) said piercing element to move to said actuated condition, relative said holding assembly, while
      3) said holding assembly is retained in said suspended position, relative said base portion; and to
   (c) a third position enabling
      1) said holding assembly to move to said released position, relative said base portion, and
      2) said piercing element to move back to said retracted position, relative said base portion, while
      3) said piercing element is retained in said actuated condition, relative said holding assembly.

20. A method for withdrawing blood from an appendage employing a self-contained blood withdrawal apparatus, said blood withdrawal apparatus including a base defining a cavity and including an upper surface having an opening into said cavity, an appendage piercing mechanism disposed in said cavity and movable between a retracted position and an extended appendage piercing position, a storage container for storing withdrawn blood coupled to said base portion and communicating with said opening, and a suction mechanism coupled to said base portion and communicating with said opening, said method comprising the steps of:

seating the appendage over the opening;

moving the piercing mechanism from the retracted position to the extended appendage piercing position to pierce the appendage and draw blood; and operating the suction mechanism to facilitate withdrawal of blood from the appendage and transport of withdrawn blood to the storage container.

21. The method for withdrawing blood as defined in claim 20, wherein, said appendage piercing mechanism includes a resilient, fluid impermeable diaphragm positioned in said cavity opening in a manner preventing said drawn blood from flowing through said opening into said cavity, and a piercing element movably disposed in said cavity, said moving step includes piercing said piercing element through a hole in said diaphragm caused by said piercing element to pierce the skin proximate said cavity opening.

22. The method for withdrawing blood as defined in claim 21, further including the step of:

withdrawing said piercing element from said hole, and urging said drawn blood to flow through said passageway means by providing said diaphragm to be sufficiently resilient to self-seal said hole and prevent blood from flowing therethrough upon retraction of said piercing element therefrom.

* * * * *

UNITED STATES PATENT AND TRADEMARK OFFICE
Certificate

Patent No. 5,662,127

Patented: September 2, 1997

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Donald H. De Vaughn, San Francisco, California; and John W. Moers, Fallbrook, California.

Signed and Sealed this Seventeenth Day of September 2002.

MICHAEL J. MILANO
*Supervisory Patent Examiner*
Art Unit 3731